United States Patent [19]
Bliss et al.

[11] Patent Number: 5,883,303
[45] Date of Patent: Mar. 16, 1999

[54] APPARATUS AND METHOD FOR PIGGING, FLOODING, AND PRESSURE TESTING PIPELINES

[76] Inventors: Brad D. Bliss; Paul D. Bliss, both of P.O. Box 19465, Houston, Tex. 77224-9465

[21] Appl. No.: 22,292
[22] Filed: Feb. 10, 1998
[51] Int. Cl.[6] .............................. G01M 3/08; G01H 3/00; F16L 55/00
[52] U.S. Cl. .......................... 73/49.1; 73/40.5 R; 73/592; 138/89
[58] Field of Search ............................... 73/40.5 R, 49.1, 73/1.72, 587, 592, 865.8; 138/89, 97, 90; 137/236.1; 251/318

*Primary Examiner*—Hezron Williams
*Assistant Examiner*—Jay L. Politzer
*Attorney, Agent, or Firm*—Kenneth A. Roddy

[57] ABSTRACT

An apparatus and method for pigging, flooding, and pressure testing pipelines utilizing a sliding sleeve valve connected at the end of a pig receiver which automatically opens upon fluid pressure in the pipeline reaching a predetermined limit allowing fluid trapped in the pipeline to escape, and is then automatically closed when the pig enters the pig receiver to allow pressure testing of the pipeline. The present apparatus and method eliminates the need and expense of a crew and/or a separate support vessel with divers or an ROV system at the downstream end of a pipeline during pigging, flooding, and pressure testing of the pipeline.

17 Claims, 3 Drawing Sheets

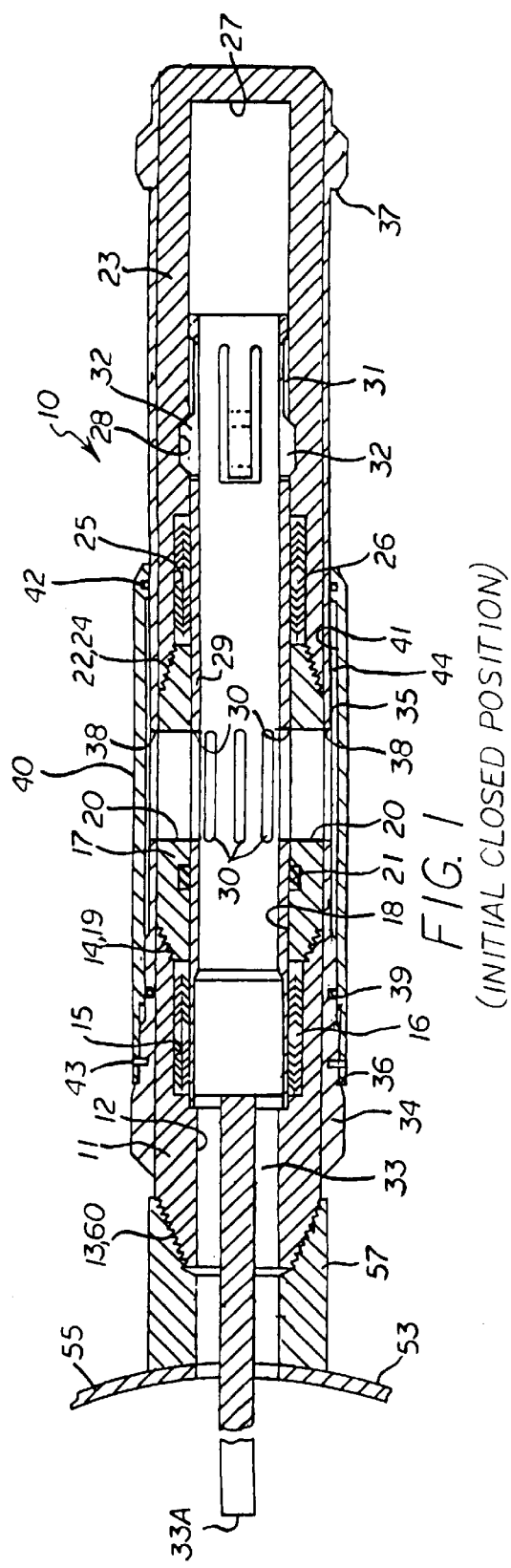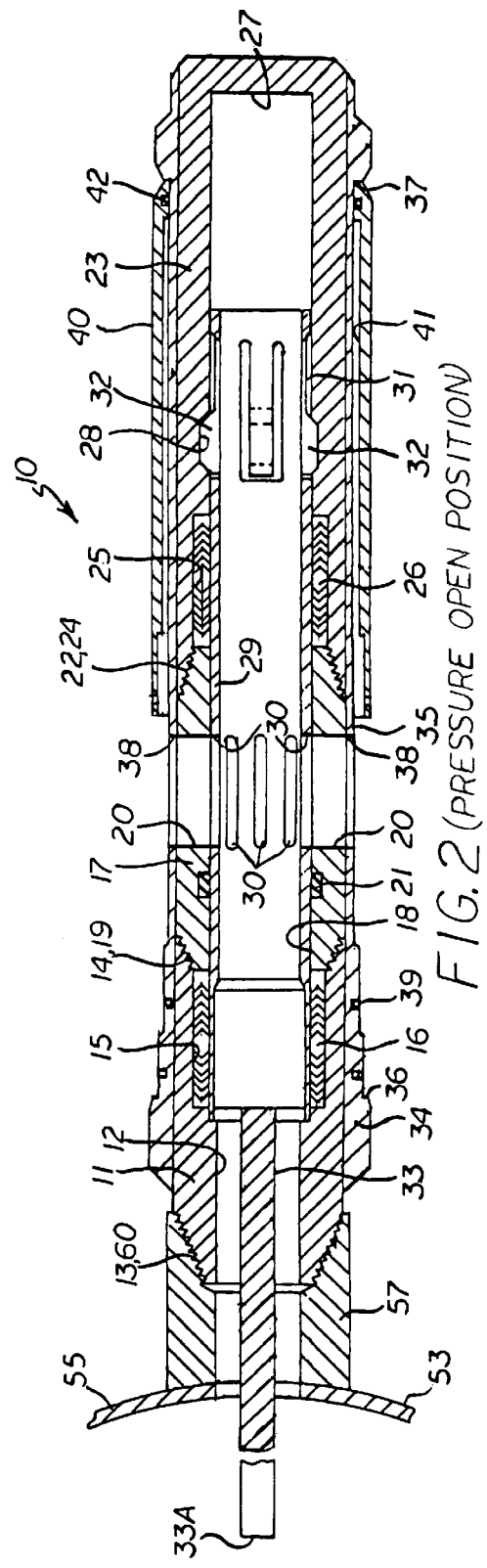

FIG. 3 (FINAL CLOSED POSITION)

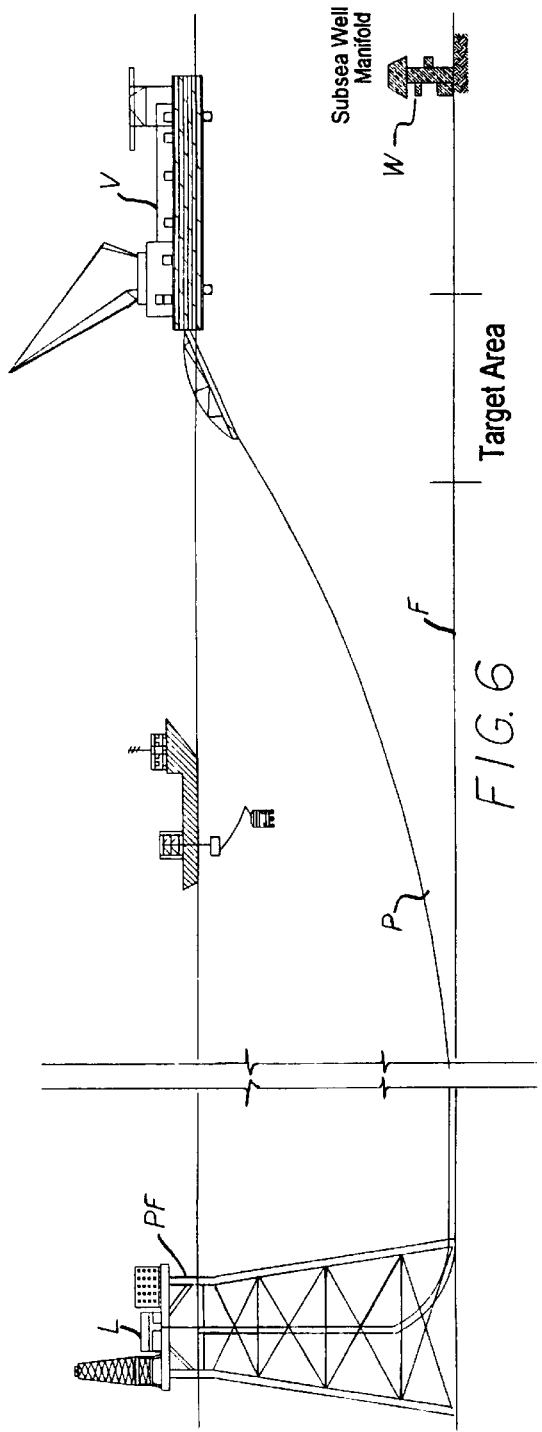
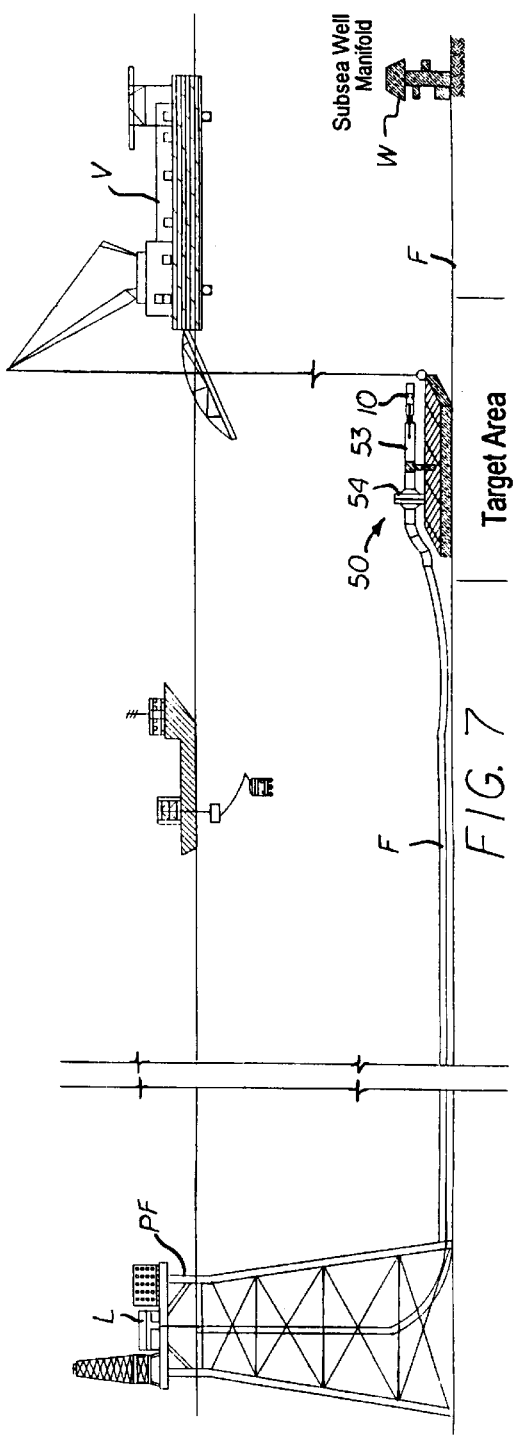

APPARATUS AND METHOD FOR PIGGING, FLOODING, AND PRESSURE TESTING PIPELINES

BACKGROUND OF THE INVENTION

1. Field of the Invention

This invention relates generally to pipeline pressure testing methods and apparatus, and more particularly to an apparatus and method for pigging, flooding, and pressure testing pipelines utilizing a sliding sleeve valve at the end of a pig receiver which automatically opens upon fluid pressure in a pipeline reaching a predetermined limit allowing fluid trapped in the pipeline to escape, and is then automatically closed when a pig enters the pig receiver to allow pressure testing of the pipeline.

2. Brief Description of the Prior Art

All hazardous liquid, natural gas, and other gas pipelines are required by government regulations to be pressure tested after construction and prior to being placed into service. Most prior art methods of pressure testing require human intervention to manually open and close a valve at the downstream end of the pipeline during the testing operation. The testing operation is considerably expensive, particularly with subsea pipelines, due to the equipment, and manpower required.

Typically, the subsea pipeline is installed on the sea floor to extend from a production facility to a downstream facility, such as an existing pipeline system or a well manifold. Conventional prior art methods of pressure testing the pipeline require a test crew on a production facility at the upstream end of the pipeline and a separate support vessel and a separate crew of divers or a remote operated vehicle (ROV) to be positioned at the submerged downstream end of the pipeline to manually operate a valve at the submerged downstream end.

In the conventional pigging, flooding, and pressure testing operation, a pig launcher is connected to the upstream end of the pipeline and a pig receiver and conventional ball valve or gate valve is connected to the downstream end. During the testing operation the support vessel or ROV system is positioned above the submerged downstream end of the pipeline. A pipeline pig is forced through the pipeline by hydraulic pressure from fluid being pumped into the upstream end behind the pig. As the pig is being forced down the pipeline, the fluid (air and/or liquid) trapped in the pipeline between the pig and the receiver becomes pressurized. One or more divers, or a ROV is sent down to open the valve to allow the trapped air or fluid to escape while fluid continues to be pumped into the pipeline until the pig enters the receiver. The valve is then manually closed and the pressure in the pipeline is increased to the required test pressure. The pressure test is then performed and monitored by the test crew on the production facility.

The present apparatus and method eliminates the need and expense of a crew, and/or a separate support vessel with divers or an ROV at the downstream end of the pipeline. This is accomplished by utilizing a sliding sleeve valve which automatically opens upon fluid pressure in the pipeline reaching a predetermined limit allowing the fluid trapped in the pipeline to escape, and is then automatically closed when the pig enters the pig receiver to allow pigging, flooding, and pressure testing of the pipeline without human intervention at the downstream end.

SUMMARY OF THE INVENTION

It is therefore an object of the present invention to provide an apparatus and method for pigging, flooding, and pressure testing pipelines which eliminates the need and expense for human intervention at the downstream end of the pipeline to carry out pigging, flooding, and pressure testing operations.

It is another object of this invention to provide an apparatus and method for pigging, flooding, and pressure testing subsea pipelines which eliminates the need and expense of a crew, and/or a separate support vessel with divers or an ROV at the downstream end of the pipeline to carry out pigging, flooding, and pressure testing operations.

Another object of this invention is to provide an apparatus and method for pigging, flooding, and pressure testing pipelines utilizing a sliding sleeve valve which is automatically opened upon fluid pressure in a pipeline reaching a predetermined limit to allow fluid trapped in the pipeline to escape, and is then automatically closed to allow pressure testing of the pipeline.

A further object of this invention is to provide an apparatus for pigging, flooding, and pressure testing pipelines which is simple in construction, and rugged and reliable in operation.

A still further object of this invention is to provide an apparatus for pigging, flooding, and pressure testing pipelines which may be constructed and placed into operation quickly and easily.

Other objects of the invention will become apparent from time to time throughout the specification and claims as hereinafter related.

The above noted objects and other objects of the invention are accomplished by the present apparatus and method utilizing a sliding sleeve valve connected at the end of a pig receiver which automatically opens upon fluid pressure in the pipeline reaching a predetermined limit allowing fluid trapped in the pipeline to escape, and is then automatically closed when the pig enters the pig receiver to allow pressure testing of the pipeline, thereby eliminating the need and expense of a crew and/or a separate support vessel with divers or an ROV system at the downstream end of a pipeline during pigging, flooding, and pressure testing of the pipeline.

BRIEF DESCRIPTION OF THE DRAWINGS

FIG. 1 is a longitudinal cross section of a sliding sleeve valve apparatus used in the pipeline testing method in accordance with the present invention, illustrated somewhat schematically and shown in an initial closed position.

FIG. 2 is a longitudinal cross section of the sliding sleeve valve apparatus shown in a pressure opened position.

FIG. 3 is a longitudinal cross section of the sliding sleeve valve apparatus shown in a final closed position.

FIG. 6 is a schematic illustration showing a subsea pipeline being laid on the sea floor.

FIG. 7 is a schematic illustration showing the termination skid positioned in the target area adjacent a subsea wellhead.

DESCRIPTION OF THE PREFERRED EMBODIMENT

Figure 4:
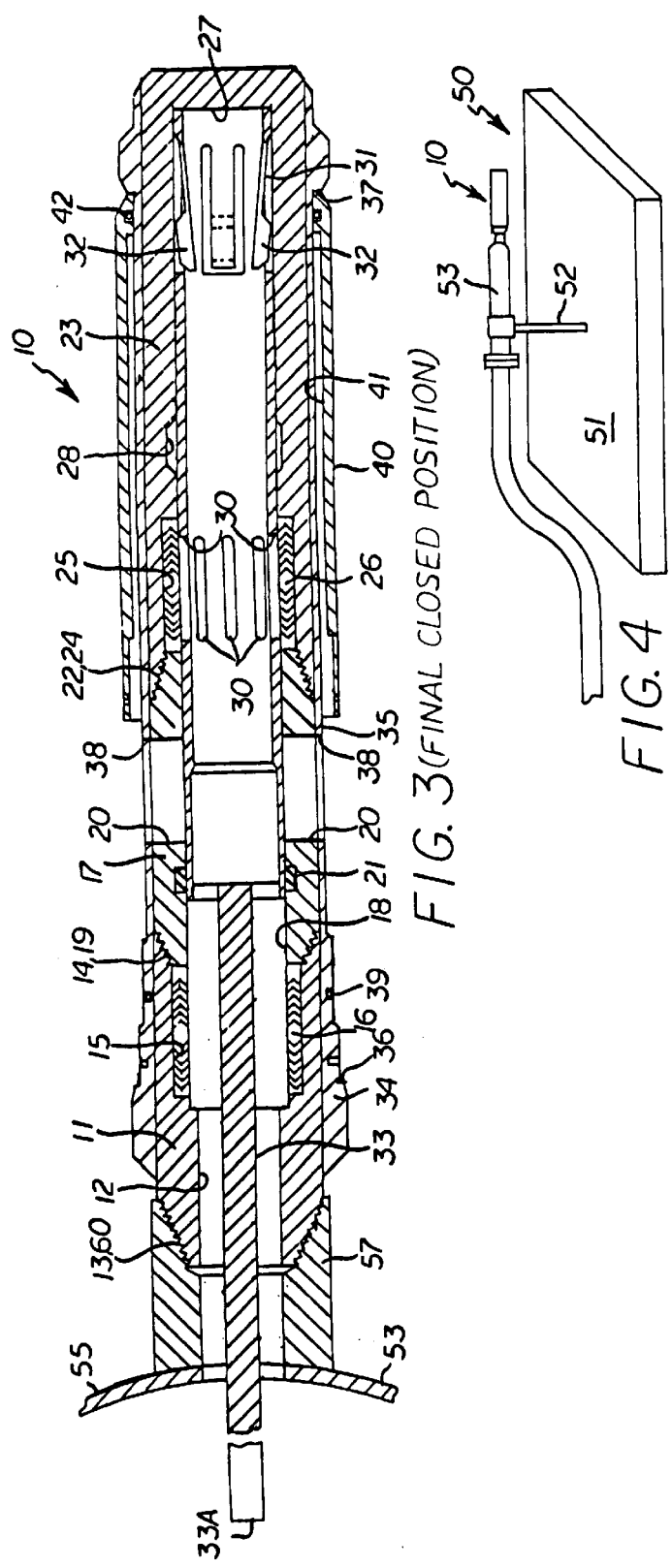
FIG. 4 is a side elevation shown somewhat schematically of a termination skid having a pig receiver and a sliding sleeve valve installed thereon.

Referring to the drawings by numerals of reference, there is shown somewhat schematically in FIGS. 1, 2, and 3, a preferred sliding sleeve valve assembly 10. In the following description, the left hand end of the valve assembly 10 (as oriented in FIG. 1) is hereinafter referred to as the upstream end and the right hand end is referred to as the downstream end.

The sliding sleeve valve assembly 10 has a cylindrical upstream seal sub 11 having a central bore 12 with external threads 13 at its upstream end and internal threads 14 at its downstream end and a larger diameter bore 15 extending inwardly from the internal threads. A packing seal element 16 such as chevron packing is installed in the larger bore 15. The external threads 13 at the upstream end of the sub 11 are threadedly engaged in a collar 57 secured to the end cap 55 of a pig receiver 53 (described below).

An intermediate sub 17 having a central bore 18 with external threads 19 at its upstream end is threadedly engaged in the internal threads 14 of the upstream packing sub 11 and compress the packing seal 16. A plurality of circumferentially spaced ports 20 extend radially through the side wall of the intermediate sub 17. A seal element 21 is installed in an annular recess in the central bore 18 of the intermediate sub 17 upstream from the ports 20 and the downstream end of the intermediate sub is provided with external threads 21.

A downstream seal sub 23 having internal threads 24 at its upstream end and a larger diameter bore 25 extending inwardly from the internal threads contains a packing seal element 26 such as chevron packing. The sub 23 is threadedly engaged in the external threads 21 at the downstream end of the intermediate sub 17 and the packing seal 26 is compressed against the downstream end of the intermediate sub 17. The downstream end of the downstream sub 23 is enclosed by an end wall 27. An annular recess 28 is formed in the interior of the sub 23 downstream from the packing seal 26.

An elongate tubular insert 29 is slidably disposed in the interior of the valve assembly 10. A plurality of circumferentially spaced ports 30 extend radially through the side wall of the insert 29. The downstream end of the insert 29 has a collet 31 with radially contractible fingers having exterior lugs 32 which are received in the recess 28 in the downstream seal sub 23 when the valve is in an initial closed position (FIG. 1). When the lugs 32 are received in the recess 28, the upstream end of the insert 29 is in fluid sealing relation with the packing seal 16 in the upstream seal sub 11 and the ports 30 are in axial alignment with the ports 20 in the side wall of the intermediate sub 17. An elongate push rod 33 is secured at one end to the upstream end of the insert 29 and its opposed end 33A projects outwardly through the upstream seal sub 11. The push rod 33 may be a solid rod or a hollow tubular member.

An elongate hollow cylindrical outer skirt 34 surrounds the exterior of the upstream, intermediate, and downstream subs 11, 17, and 23, respectively, and is secured thereto in fluid sealed relation to form a stationary unit. The exterior of the outer skirt 34 and has a reduced diameter exterior portion 35 intermediate its upstream and downstream ends and radial shoulders 36 and 37 at each end of the reduced diameter. A plurality of circumferentially spaced ports 38 extend radially through the reduced diameter portion of the skirt 34. The ports 38 are aligned with the ports 20 of the intermediate sub 17. An O-ring seal 39 is installed on the exterior of the skirt 34 upstream from the ports 38.

An outer sliding sleeve 40 having a central bore 41 extending inwardly from its upstream end and an O-ring seal 42 installed in its downstream end is slidably received on the exterior of the outer skirt 34. The outer sliding sleeve 40 is temporarily secured over the ports 38 in the outer skirt 34 by at least one shear pin 43. In the pinned condition, the interior of the sliding sleeve 40 forms an annulus 44 between the interior of the sliding sleeve and the exterior of the outer skirt 34 which is sealed at each end by the O-rings 39 and 42 to prevent fluid communication between the interior and exterior valve assembly 10.

The sliding sleeve valve assembly 10 is movable between an initial closed position (FIG. 1), a pressure opened position (FIG. 2), and a final mechanically closed position (FIG. 3), as described below.

In the initial closed position (FIG. 1), the collet lugs 32 of the insert 29 are spring biased radially into the recess 28 of the downstream sub 23 and the ports 30 of the insert 29, the ports 20 of the intermediate sub 17, and the ports 38 of the outer skirt 34 are aligned and positioned between the packing seals 16 and 26 at each end of the intermediate sub 17. The outer sliding sleeve 40 is secured by the shear pin 43 over the ports 38 in the outer skirt 34 and the annulus 44 is sealed by the O-rings 39 and 42 to prevent fluid communication between the interior and exterior of the valve and pipeline.

As shown in the pressure opened position in FIG. 2, when the internal pressure in the pipeline and valve 10 exceeds a predetermined value, the pressure in the annulus 44 acts on the interior of the sliding sleeve 40, developing a force sufficient to shear the shear pin 43 and cause the sliding sleeve to slide in the downstream direction relative to the outer skirt 34, respectively, and the aligned ports 30, 20, and 38 of the insert 29, intermediate sub 17, and outer skirt 34 are exposed, allowing fluid to escape from the interior of the pipeline and valve.

Figure 5:
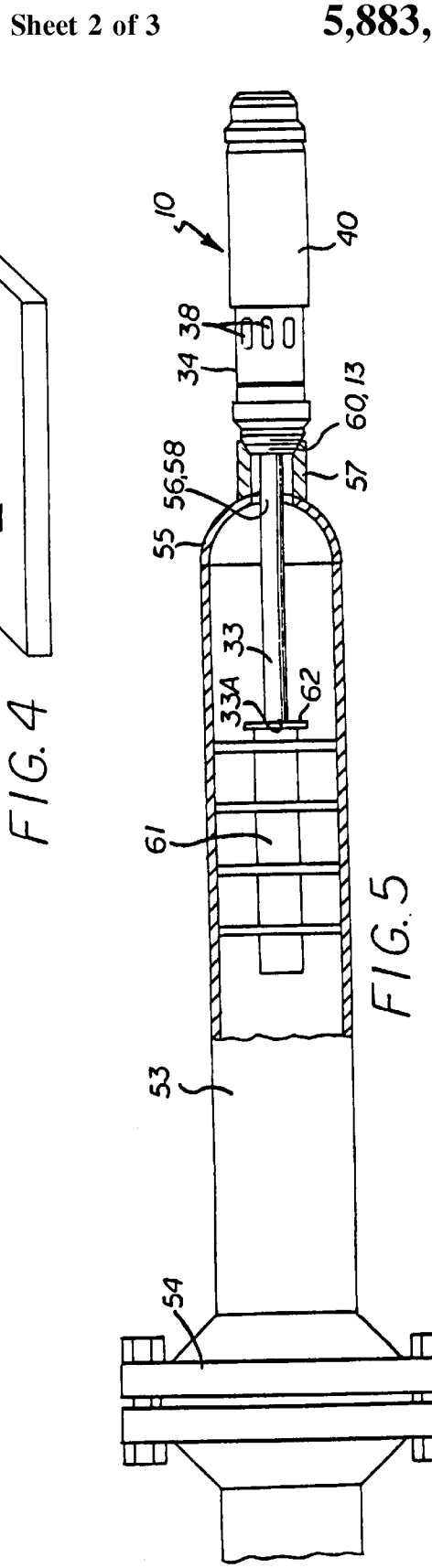
FIG. 5 is a side elevation of the pig receiver shown in partial cross section.

The final closed position (FIG. 3) of the valve 10 is achieved mechanically when the force acting on a movable plug member having an exterior surface which forms a movable fluid sealing relation with the interior surface of said pipeline, such as a pipeline pig 61 is applied to the push rod 33 and insert 29 of the valve (FIG. 5). The force is transmitted through the insert 29 to the collet 31 at its downstream end causing the lugs 32 to retract radially inward and allowing the insert 29 to slide in the downstream direction relative to the subs 11, 17, and 23 such that the ports 30 in its side wall are no longer aligned with the ports 20 of the intermediate sub 17 and the ports 38 of the outer skirt 34. In this position, the upstream end of the insert 29 is in sealing relation with the packing seal 26 in the downstream sub 23 and the side wall of the insert prevents internal pressure from passing through the ports 20 and 38 in the intermediate sub 17 and outer skirt 34, respectively. Thus, in the final closed position the valve is once again closed and prevents fluid communication between the interior and exterior of the valve and pipeline, and the pipeline can then be pressure tested.

In FIGS. 4, 6, and 7, the apparatus is shown and described as being installed at the end of a subsea pipeline as an example, however, it should be understood that the apparatus may be installed on, and the method carried out on, pipelines which are above-water as well as subsea pipelines.

FIG. 4 shows a termination skid 50 having a base platform 51 with a support member 52 extending vertically upwardly a distance therefrom and a pig receiver 53 secured generally horizontally to the upper end of the support member, which may be used in subsea pipeline applications. On pipelines which are above-water, other conventional means may be used to support the pig receiver in a generally horizontal position.

As best seen in FIG. 5, the pig receiver 53 is a hollow cylindrical member having a radial flange 54 at its upstream end and an end cap 55 secured to its downstream end. A central bore 56 extends through the end cap 55. A collar 57 having a central bore 58 and internal threads 60 at its downstream end is secured to the exterior of the end cap 55 with the bores 58 and 56 in axial alignment. Referring again to FIG. 1, the push rod 33 extends through the bores 58 and 56 of the collar 57 and end cap 55 and protrudes a distance into the interior of the pig retainer 53. Optionally, a seal element (not shown) may be installed in the central bore 58 of the collar 57 through which the push rod slides in a sealing relation.

In FIG. 5, a movable plug member having an exterior surface which forms a movable fluid sealing relation with the interior surface of the pipeline, such as a pipeline pig 61, is shown received in the interior of the pig retainer 53. This takes place after the initially closed valve has been opened by the internal pressure in the pipeline and valve. The pipeline pig 61 may be of conventional construction, with the exception of a rigid contact plate 62 secured to its forward end which engages the protruding end of the push rod 33 to move the valve 10 to the final closed position, as explained hereinafter.

Referring now to FIGS. 6 and 7, the subsea pipeline P is laid out on the sea floor F by a pipe laying vessel V to extend from a production facility PF such as an offshore production platform to a target area adjacent a downstream facility, such as an existing pipeline system or a subsea wellhead manifold W. Prior to laying the final section of the pipeline, a flange is secured to the free end of the pipeline and is connected with the flange 54 of the pig receiver 53 of the termination skid 50 (FIG. 5) to form a fluid-tight connection and the termination skid is lowered onto the sea floor F in the target area adjacent the downstream facility W. Thus, the pipeline P is installed in a dry state (void of water).

After the pipeline P and termination skid 50 is placed on the sea floor F in the target area, the movable plug or pipeline pig is installed in a pig launcher L on the production facility PF and the launcher is connected to the upstream end of the pipeline P. The flood pumping and pressure testing equipment is connected to the pig launcher on the production facility PF.

Water is then pumped into the barrel of the pig launcher L and water is pumped into the pipeline P behind the pig. The water and pressure in the pipeline forces the pig to move downstream toward the subsea termination skid 50. As the pipeline begins to fill up with water, the pressure in the pipeline increases. As the pig is being forced down the pipeline, the sliding sleeve valve 10 is in the initially closed position as shown in FIG. 1 and the end of the valve is sealed by the end wall 27 at its outer end. The pig, and water behind it, compresses the fluid trapped downstream in the pipeline P and valve 10 in front of the pig due to the sealed end 27 of the sliding sleeve valve.

When the internal pressure in the pipeline P and interior of the valve 10 exceeds a predetermined amount, the shear pin 43 on the sliding sleeve valve 10 shears, and the pressure forces the sliding sleeve 40 to slide in the downstream direction which exposes the aligned ports 20, 30, and 38 and allows the compressed fluid trapped in the pipeline to escape, as shown in FIG. 2 and explained above. Water continues to be pumped into the pipeline P until the pig is received in the interior of the pig receiver 53 (FIG. 5).

When the pig 61 enters the pig receiver 53, the contact plate 62 at the forward end of the pig engages the protruding end of the push rod 33. The upstream force acting on the pig 61, the push rod 33 and the insert 29 causes the collet finger lugs 32 to retract and the insert slides in the downstream direction such that its communication ports 30 move past the packing seal 16, as shown in FIG. 3 and described above. The movement of the insert 29 closes the sliding sleeve valve 10 and seals off the pipeline. With the pipeline P and the now closed valve flooded with water, the pressure test is performed by the test crew on the production facility PF for the designed pressure and duration.

While this invention has been described fully and completely with special emphasis upon a preferred embodiment, it should be understood that within the scope of the appended claims the invention may be practiced otherwise than as specifically described herein.

For example, the apparatus may be installed on, and the method carried out on, pipelines which are above-water. In this modification, other conventional means may be used to support the pig receiver in a generally horizontal position and it would not be necessary to provide the previously described termination skid or base platform having a vertical support member.

We claim:

1. A method for pigging, flooding, and pressure testing a pipeline without human intervention at the downstream end of the pipeline, comprising the steps of:

providing a hollow tubular receiver at the downstream end of a pipeline to be pressure tested, the interior of said tubular receiver being in fluid communication with the interior of said pipeline;

providing valve means on said receiver in fluid communication with the interior of said receiver and said pipeline, said valve means having an exhaust port for conducting fluid to the exterior thereof and being moved from an initial closed position to an opened position responsive to fluid pressure in said pipeline and said receiver reaching a predetermined limit to allow fluid trapped in said pipeline, said receiver, and said valve means to escape to the exterior through said exhaust port, and said valve means having an actuator associated with said receiver for mechanically moving said valve means from said opened position to a final closed position upon a mechanical force of predetermined magnitude acting thereon to close said exhaust port;

providing a movable plug member having an exterior surface which forms a movable fluid sealing relation with the interior surface of said pipeline;

placing said movable plug member in the upstream end of said pipeline and applying a fluid force behind said movable plug member to move it along the pipeline interior to the downstream end to be received in said receiver and thereby increase the fluid pressure in said pipeline, said receiver, and said valve means, sufficient to move said valve means from said initial closed position to said opened position;

maintaining said fluid force behind said movable plug member to cause said plug member to move into said receiver and mechanically engage said actuator with a force of sufficient magnitude to move said valve means to said final closed position, thereby closing said exhaust port; and thereafter increasing fluid pressure in said pipeline with said valve means in said final closed position to carry out pressure testing of said pipeline.

2. An apparatus for pigging, flooding, and pressure testing a pipeline without human intervention at the downstream end of the pipeline, comprising:

a hollow tubular receiver connected to the downstream end of a pipeline to be pressure tested, the interior of said tubular receiver being in fluid communication with the interior of said pipeline;

valve means on said receiver in fluid communication with the interior of said receiver and said pipeline, said valve means having an exhaust port for conducting fluid to the exterior thereof and being moved from an initial closed position to an opened position responsive to fluid pressure in said pipeline and said receiver reaching a predetermined limit to allow fluid trapped in said pipeline, said receiver, and said valve means, to escape to the exterior through said exhaust port, and said valve means having an actuator associated with said receiver for mechanically moving said valve means from said opened position to a final closed position upon a mechanical force of predetermined magnitude acting thereon to close said exhaust port; and a movable plug member having an exterior surface which forms a movable fluid sealing relation with the interior surface of said pipeline; wherein said movable plug member is placed in the upstream end of said pipeline and a fluid force is applied behind said movable plug member to move it along the pipeline interior to the downstream end to be received in said receiver and thereby increase the fluid pressure in said pipeline, said receiver, and said valve means, sufficient to move said valve means from said initial closed position to said opened position; and said fluid force is maintained behind said movable plug member to cause said movable plug member to move into said receiver and mechanically engage said actuator with a force of sufficient magnitude to move said valve means to said final closed position, thereby closing said exhaust port; and said valve means remains in said final closed position while fluid pressure in said pipeline is increased to carry out pressure testing of said pipeline.

3. The apparatus according to claim 2, wherein
said movable plug is a pipeline pig.

4. The apparatus according to claim 2, wherein
said valve means is a sliding sleeve valve assembly comprising:

an elongate cylindrical body having an upstream end and an enclosed downstream end with a central bore in fluid communication with the interior of said receiver extending from said upstream end terminating at said enclosed downstream end, a plurality of circumferentially spaced exhaust ports extending radially through said body, and an annular recess formed in the interior of said body;

an elongate tubular insert slidably disposed in said body central bore for axial movement relative thereto, said insert having a plurality of circumferentially spaced ports extending radially through its side wall, and outwardly flexible means at one end movable in a radially expandible direction to engage said annular recess; and a cylindrical tubular outer skirt slidably received on the exterior of said valve body, said skirt temporarily secured by shearable means to said valve body to surround said exhaust ports.

5. The apparatus according to claim 4, wherein
in said initially closed position, said insert outwardly flexible means is radially expanded into engagement with said annular recess with said insert ports axially aligned with said body exhaust ports; and said outer skirt is maintained on said valve body surrounding said aligned exhaust ports and insert ports by said shearable means such that fluid and pressure in said pipeline, said receiver, and said valve body downstream from said movable plug member is prevented from escaping; and upon fluid pressure in said pipeline, said receiver, and said valve body exceeding a predetermined pressure, said shearable means shears apart and said skirt moves relative to said valve body to allow fluid and pressure in said pipeline, said receiver and said valve body downstream from said movable plug member to escape to the exterior through said aligned exhaust ports and insert ports; and thereafter fluid pressure behind said movable plug member moves said movable plug member downstream into said receiver to mechanically engage said actuator with a force of sufficient magnitude to disengage said insert outwardly flexible means from said annular recess and move said insert axially relative to said valve body such that said body exhaust ports and said insert ports are closed off by said insert to prevent fluid and pressure in said pipeline, said receiver and said valve body from escaping the exterior through said exhaust ports and said insert ports.

6. The apparatus according to claim 4, wherein
said actuator is an elongate rod connected at one end end to said insert and extending slidably through said valve body and having an opposed end disposed in said receiver to engage said movable plug member after it enters said receiver and move said insert axially relative to said valve body.

7. The apparatus according to claim 6, wherein
said movable plug is a pipeline pig having a rigid forward end configured to engage said opposed end of said elongate rod.

8. The apparatus according to claim 4, wherein
said insert outwardly flexible means comprises collet members.

9. The apparatus according to claim 4, wherein
said shearable means comprises at least one shear pin extending between said skirt and said valve body.

10. The apparatus according to claim 2, wherein
said valve means is a sliding sleeve valve assembly comprising:

an elongate cylindrical body having an upstream end and an enclosed downstream end with a central bore extending from said upstream end terminating at said enclosed downstream end, first and second seal means on the interior of said body spaced a distance inwardly from said upstream end and said enclosed downstream end, respectively, a plurality of circumferentially spaced exhaust ports extending radially through said body disposed intermediate said first and second seal means, an annular recess formed in the interior of said body downstream from said second seal means, and third seal means on the exterior of said valve body spaced longitudinally from said exhaust ports, said upstream end connected to said receiver with said central bore in fluid communication with the interior of said receiver;

an elongate tubular insert slidably disposed in said body central bore for axial movement relative thereto, said insert having an upstream end and a downstream end, a plurality of circumferentially spaced ports extending radially through its side wall intermediate its said upstream and downstream ends, and outwardly flexible means at said insert downstream end movable in a radially expandible direction;

a cylindrical tubular outer skirt slidably received on the exterior of said valve body a distance above said stop means, said skirt having a first end temporarily secured by shearable means to said valve body and sealingly engaged with said third seal means in the secured condition, an interior surface defining an annulus surrounding said exhaust ports, a reduced diameter interior portion at a second end of said skirt defining a radial shoulder at one end of said annulus, and fourth seal means at a second end said annulus movable in fluid sealing relation with the exterior surface of said valve body; wherein in said initially closed position, said insert outwardly flexible means is radially expanded into engagement with said annular recess with said insert ports axially aligned with said body exhaust ports and said insert is engaged in fluid sealing relation with said first and said second seal means; and said outer skirt is maintained on said valve body surrounding said aligned exhaust ports and insert ports by said shearable means and fluid and pressure in said pipeline, said receiver, said valve body, and said skirt annulus downstream from said movable plug member is prevented from escaping by said third and fourth seal means; and upon fluid pressure in said pipeline, said receiver, said valve body, and said skirt annulus downstream from said movable plug member exceeding a predetermined pressure, said shearable means shears apart and said skirt moves relative to said valve body to disengage said skirt from said third seal means and allow fluid and pressure in said pipeline, said receiver and said valve body downstream from said movable plug member to escape to the exterior through said aligned exhaust ports and insert ports; and thereafter fluid pressure behind said movable plug member moves said movable plug member downstream into said receiver to mechanically engage said actuator with a force of sufficient magnitude to disengage said insert outwardly flexible means from said annular recess and move said insert axially relative to said valve body such that said body exhaust ports and said insert ports are closed off by said insert and said insert is sealingly engaged with said first and said second seal means to prevent fluid and pressure in said pipeline, said receiver and said valve body from escaping the exterior through said exhaust ports and insert ports.

11. A valve apparatus in combination with a pipeline pig receiver for pigging, flooding, and pressure testing a pipeline without human intervention at the downstream end of the pipeline, comprising:

a hollow tubular pipeline pig receiver connected at an upstream end to the downstream end of a pipeline to be pressure tested, the interior of said receiver being in fluid communication with the interior of said pipeline;

valve means on a downstream end of said receiver in fluid communication with the interior of said receiver and said pipeline, said valve means having an exhaust port for conducting fluid to the exterior thereof and being moved from an initial closed position to an opened position responsive to fluid pressure in said pipeline and said receiver reaching a predetermined limit to allow fluid trapped in said pipeline, said receiver, and said valve means, to escape to the exterior through said exhaust port, and said valve means having an actuator associated with said receiver for mechanically moving said valve means from said opened position to a final closed position upon a mechanical force of predetermined magnitude acting thereon to close said exhaust port; and a pipeline pig member having an exterior surface which forms a movable fluid sealing relation with the interior surface of said pipeline; wherein said pig member is placed in the upstream end of said pipeline and a fluid force is applied behind said pig member to move it along the pipeline interior to the downstream end to be received in said receiver and thereby increase the fluid pressure in said pipeline, said receiver, and said valve means, sufficient to move said valve means from said initial closed position to said opened position; and said fluid force is maintained behind said pig member to cause said pig member to move into said receiver and mechanically engage said actuator with a force of sufficient magnitude to move said valve means to said final closed position, thereby closing said exhaust port; and said valve means remains in said final closed position while fluid pressure in said pipeline is increased to carry out pressure testing of said pipeline.

12. The apparatus according to claim 11, wherein said valve means is a sliding sleeve valve assembly comprising:

an elongate cylindrical body having an upstream end and an enclosed downstream end with a central bore in fluid communication with the interior of said receiver extending from said upstream end terminating at said enclosed downstream end, a plurality of circumferentially spaced exhaust ports extending radially through said body, and an annular recess formed in the interior of said body;

an elongate tubular insert slidably disposed in said body central bore for axial movement relative thereto, said insert having a plurality of circumferentially spaced ports extending radially through its side wall, and outwardly flexible means at one end movable in a radially expandible direction to engage said annular recess; and a cylindrical tubular outer skirt slidably received on the exterior of said valve body, said skirt temporarily secured by shearable means to said valve body to surround said exhaust ports.

13. The apparatus according to claim 12, wherein in said initially closed position, said insert outwardly flexible means is radially expanded into engagement with said annular recess with said insert ports axially aligned with said body exhaust ports; and said outer skirt is maintained on said valve body surrounding said aligned exhaust ports and insert ports by said shearable means such that fluid and pressure in said pipeline, said receiver, and said valve body downstream from said movable plug member is prevented from escaping; and upon fluid pressure in said pipeline, said receiver, and said valve body exceeding a predetermined pressure, said shearable means shears apart and said skirt moves relative to said valve body to allow fluid and pressure in said pipeline, said receiver and said valve body downstream from said pig member to escape to the exterior through said aligned exhaust ports and insert ports; and thereafter fluid pressure behind said pig member moves said pig member downstream into said receiver to mechanically engage said actuator with a force of sufficient magnitude to disengage said insert outwardly flexible means from said annular recess and move said insert axially relative to said valve body such that said body exhaust ports and said insert ports are closed off by said insert to prevent fluid and pressure in said pipeline, said receiver and said valve body from escaping the exterior through said exhaust ports and said insert ports.

14. The apparatus according to claim 12, wherein said actuator is an elongate rod connected at one end end to said insert and extending slidably through said valve body and having an opposed end disposed in said receiver to engage said pig member after it enters said receiver and move said insert axially relative to said valve body.

15. The apparatus according to claim 14, wherein said pig member has a rigid forward end configured to engage said opposed end of said elongate rod.

16. The apparatus according to claim 12, wherein said insert outwardly flexible means comprises collet members.

17. The apparatus according to claim 12, wherein said shearable means comprises at least one shear pin extending between said skirt and said valve body.

* * * * *